United States Patent [19]
Tolman et al.

[11] Patent Number: 5,663,175
[45] Date of Patent: Sep. 2, 1997

[54] PRODRUGS OF HERPES TK INHIBITORS

[75] Inventors: Richard L. Tolman, Warren, N.J.;
John D. Karkas, New York, N.Y.;
Derek Von Langen, Fanwood;
Malcolm MacCoss, Freehold, both of N.J.

[73] Assignee: Merck & Co. Inc., Rahway, N.J.

[21] Appl. No.: 353,475

[22] Filed: Dec. 9, 1994

[51] Int. Cl.$^6$ ....................................... A61K 31/52
[52] U.S. Cl. .................. 514/262; 514/261; 514/265; 514/931; 514/934; 544/276; 544/277; 544/267
[58] Field of Search .................. 514/262, 261, 514/265, 931, 934; 544/276, 277, 267

[56] References Cited

U.S. PATENT DOCUMENTS

| 4,782,062 | 11/1988 | Tolman et al. | 514/262 |
| 5,137,724 | 8/1992 | Balzarini et al. | 514/934 |

FOREIGN PATENT DOCUMENTS 9205180  2/1992  WIPO.

OTHER PUBLICATIONS

Klein et al., Antiviral Research, vol. 14, pp. 207–214, (1990).
Ashton, et al., "A Potent, Selective, Non–Substrate Inhibitor of HSV–1 Thymidine Kinase:", Nucleosides & Nucleotides, 8(5&6), pp. 1157–1158 (1989).
Bourne, et al., "Assessment of a Selective Inhibitor of Herpes Simples Virus Thymidine Kinase . . . ", Antimicrobial Agents and Chemo., vol. 36, No. 9, pp. 2020–2024, Sep. 1992.
Leib, et al., "Specific Inhibitors of Herpes Simplex Virus Thymidine Kinase Diminish Reactivation . . . ", Antimocrobial Agents and Chemo., vol. 34, No. 6, pp. 1285–1286, Jun. 1990.
Nsiah, et al., "Suppression of Herpes Simplex Virus Type 1 Reactivation from Latency . . . ", Antimicrobial Agents and Chemo., vol;. 34, No. 8, pp. 1551–1555, Aug. 1990.
Klein, et al., "Effect of a Thymidine Kinase Inhibitor (L–653,180) on Antiviral Treatment . . . ", Antiviral Research 14, pp. 207–214 (1990).
Jacobson, et al., "Herpes Simplex Virus Thymidine Kinase and Specific Stages of Latency in Murine Trigeminal Ganglia", J. of Vir., pp. 6903–6908, vol. 67, No. 11, Nov. 1993.
Spadari, et al., "L–Thymidine is Phosphorylated by Herpes Simplex Virus Type 1 Thymidine Kinase and Inhibits Viral Growth", J. of Med. Chem., pp. 4214–4220, 35, (1992).

Primary Examiner—James O. Wilson
Attorney, Agent, or Firm—Sylvia A. Ayler; Mark R. Daniel

[57] ABSTRACT

Certain prodrugs such as

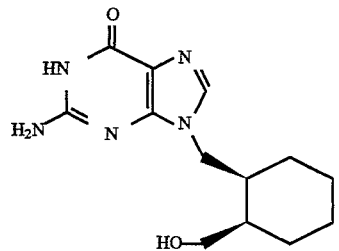

are useful in the inhibition of herpes virus thymidine kinase, the prevention or treatment of recurrent infection by herpes virus, either as compounds, pharmaceutically acceptable salts, pharmaceutical composition ingredients, whether or not in combination with other antivirals, immunomodulators, antibiotics or vaccines. Methods of preventing or treating recurrent infection by herpes virus are also described.

6 Claims, No Drawings

PRODRUGS OF HERPES TK INHIBITORS

BACKGROUND OF THE INVENTION

Herpes virus is the etiological agent in a variety of infections, including diseases of the skin, mucous membranes, eye, or nervous system. A characteristic feature of herpes infection is its reactivation from latent form, leading to recurrence of symptoms, e.g., sores, long after initial infection.

There is no effective or clinically acceptable treatment of herpes to prevent reactivation of latent virus. Acyclovir (2-Amino-1,9-dihydro-9-[(2-hydroxyethoxy)methyl]-6H-purin-6-one) is prescribed in megadoses on a prophylactic basis for individuals with frequent recurrences. By definition, since acyclovir is a prodrug for a triphosphate derivative which inhibits the viral polymerase, this drug can only act to kill the virus after reactivation has already occurred. Thymidine kinase ("TK") inhibitors are useful for interfering with the reactivation process. TK inhibitors are also useful for depleting the number of cells with reactivatable latent virus.

Previously known TK inhibitors have one or more of the following disadvantages: biochemical actions other than TK inhibition with resulting undesired side effects; metabolic breakdown products that are genotoxic; insolubility, which complicates evaluation in animals; or low potency.

The first principal finding of the present invention is that the enantiomer L-758,340 is a potent inhibitor of herpes thymidine kinase.

Applicants have discovered that the enantiomer

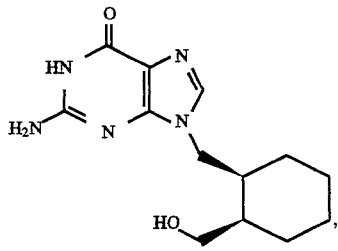

L-758340 IC$_{50}$ = 102 nM [1S,2R]

is substantially more active as an inhibitor of herpes thymidine kinase than its enantiomer

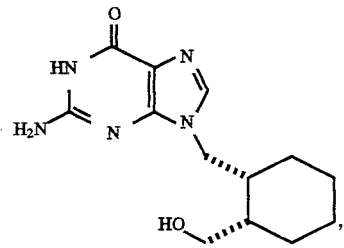

L-758341 IC$_{50}$ = 763 nM. [1R,2S]

The racemate of L-758,340 and L-758,341 is known, see e.g., U.S. Pat. No. 4,782,062.

A second principal finding of the present inventions is that certain prodrug types of L-758,340 have advantages in pharmacodynamics and physical properties, and are useful in the treatment or prevention of reactivation of herpes virus infections.

Applicants provide a novel synthetic route for the enantio selective synthesis of L-758,340. The key step in the synthesis is a lipase based hydrolysis of a prochiral diacetate. This hydrolysis gives excellent chemical yields and stereo selectivity but also can be easily scaled up to produce large quantities of optically active material.

BRIEF DESCRIPTION OF THE INVENTION

Compounds of Formula I, as herein defined, are disclosed. These compounds are useful in the inhibition of herpes thymidine kinase, and thereby in the prevention of recurrent, latent herpes virus, either as compounds, pharmaceutically acceptable salts (when appropriate), pharmaceutical composition ingredients, whether or not in combination with other antivirals, anti-infectives, immunomodulators, antibiotics or vaccines. Methods of preventing herpes virus recurrences are disclosed.

DETAILED DESCRIPTION OF THE INVENTION AND PREFERRED EMBODIMENTS

This invention is concerned with compounds of Formula I, combinations thereof, or pharmaceutically acceptable salts thereof, in the inhibition of herpes thymidine kinase and the prevention of recurrent infection by herpes virus. Compounds of Formula I are defined as follows:

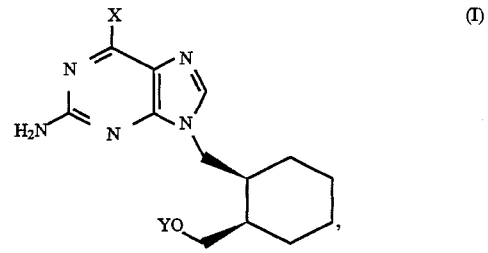

(I)

or tautomers thereof, or a pharmaceutically acceptable salt or hydrate thereof, wherein X is H, —NH$_2$, —OH, NHR or OR wherein R is C$_{1-4}$alkyl, Y is H or phosphoryl.

One embodiment of the present invention are the compounds

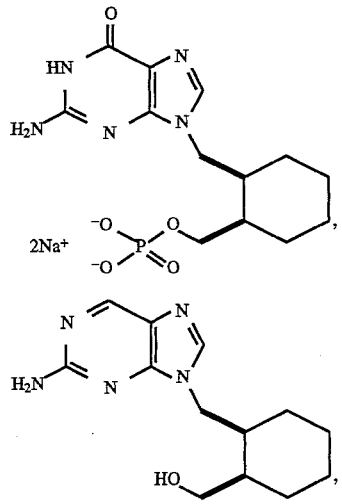

-continued or

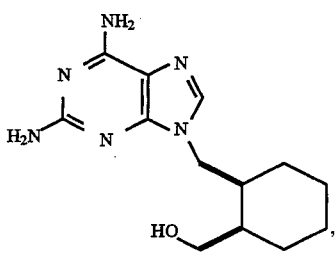

or pharmaceutically acceptable salt or hydrate treated. One preferred embodiment is

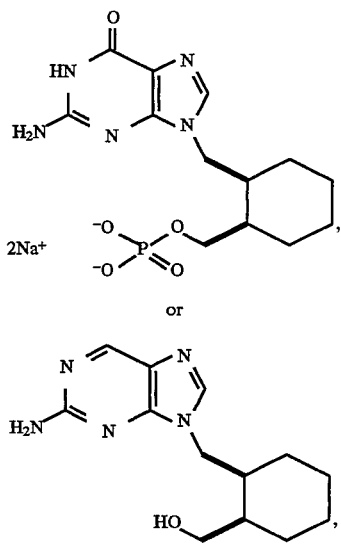

or

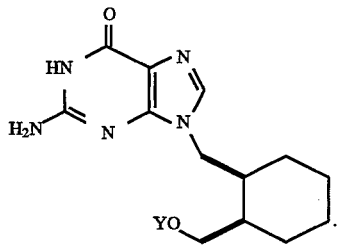

or a pharmaceutically acceptable salt or hydrate thereof.

When any variable (e.g., R) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched-, cyclo- and straight-chain saturated aliphatic hydrocarbon groups having the specified number of carbon atoms.

Tautomers of Formula I include, for example, when X=OH, the corresponding guanosine base:

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, rosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The compounds of the present invention can be synthesized by the following methods.

SCHEME 1

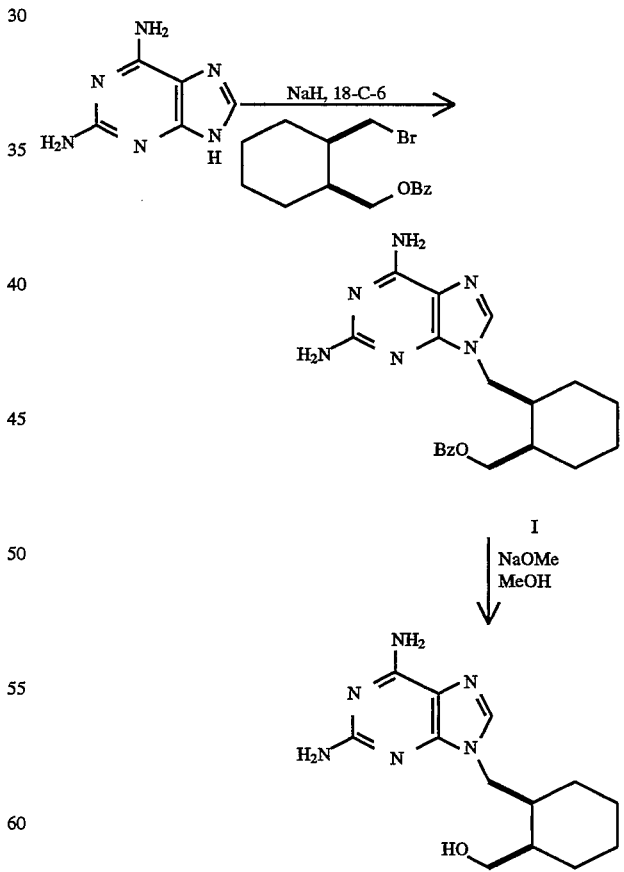

Under Scheme 1, the artion of 2,6-diaminopurine is formed under phase transfer conditions (18-crown-6, sodium hydride) and alkylated with a suitably protected alkyl halide. The protecting group is removed under normal conditions to give the desired product II.

SCHEME 2

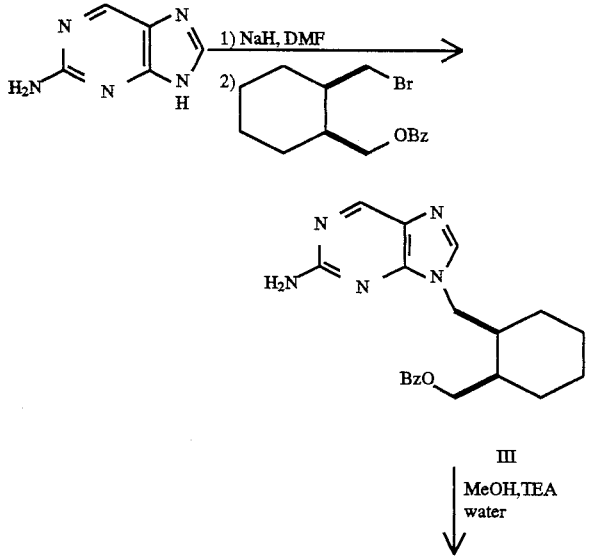

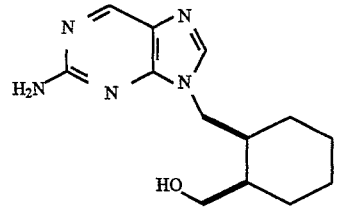

The anion of 2-aminopurine according to Scheme 2 is formed using a suitable hydride reagent, usually sodium hydride in DMF, and then alkylated with a suitably protected alkylhalide. The protecting group is removed under conditions to give the desired product IV.

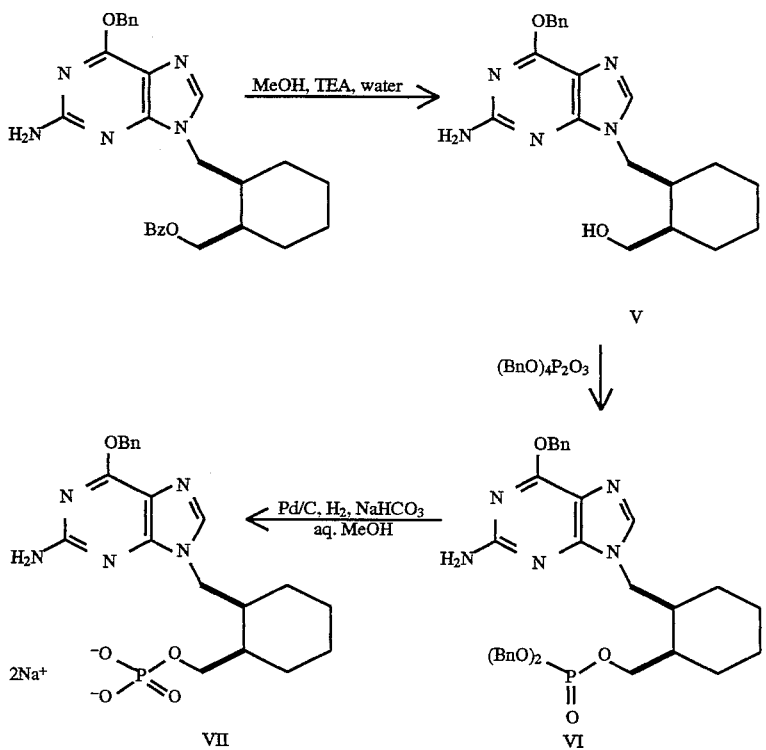

In Scheme 3, 2-amino-9-{[(Z)-2-benzoyloxymethyl) cyclohexyl]methyl}-6-benzyloxypurine is prepared according to the method of Ashton et al., Nucleosides &

Nucleotides, 8, 1157 (1989), and the benzoate is removed under standard conditions. The anion of the hydroxyl function is formed using t-butylmagnesium bromide and phosphorylated using tetrabenzylpyrophosphate. The three benzyloxy groups are removed simultaneously using standard hydrogenation conditions in the presence of sodium bicarbonate to yield the desired disodium salt.

mono-deprotected to yield the optically-active mono-acetate. The hydroxyl function is converted to the primary bromide under standard condition and the bromide is used to alkylate the anion of a suitable purine derivative. Hydrogenation removes the olefin from the cyclohexyl moiety and deprotects the purine nucleus. Removal of the acetate under normal conditions gives the desired optically active product.

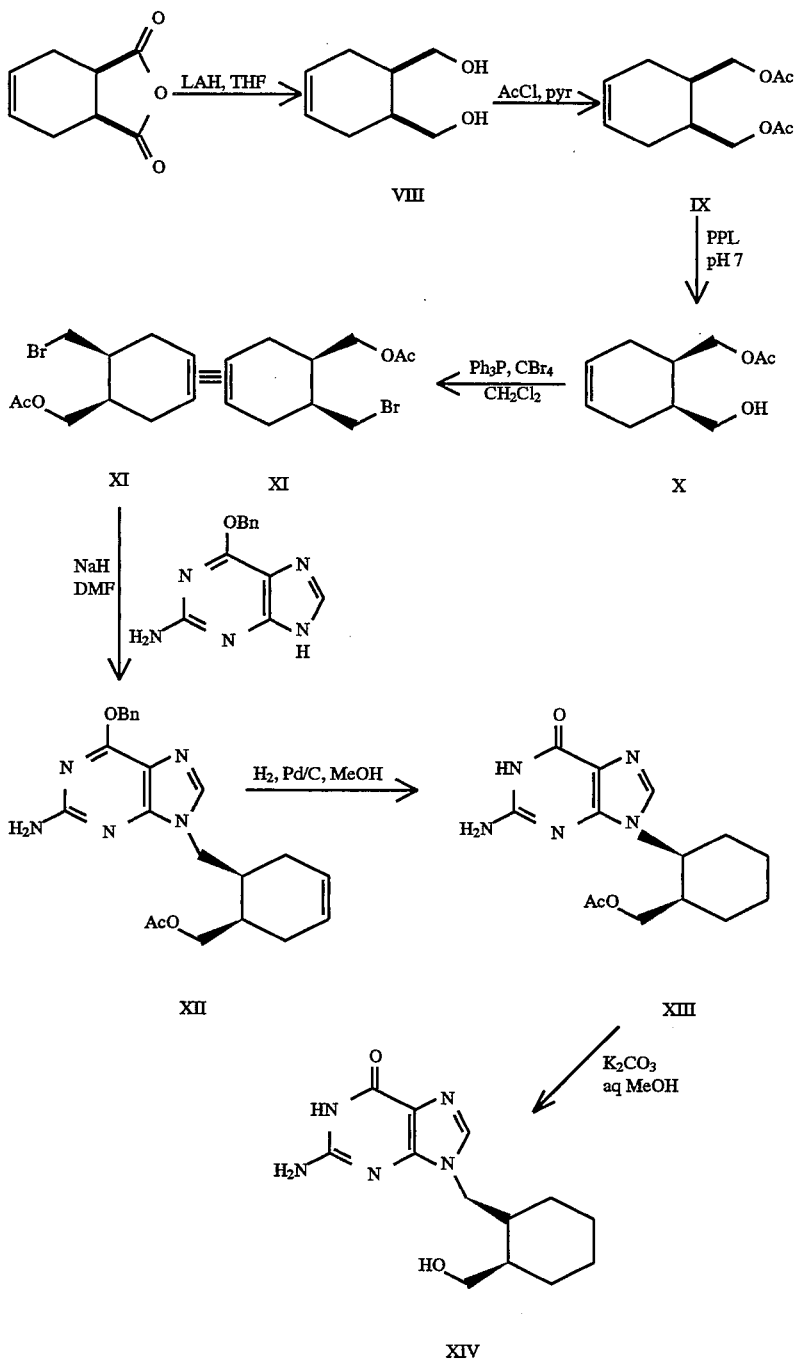

SCHEME 4

Commercially available phthalic anhydride in Scheme 4 is reduced to the meso diol using lithium aluminum hydride. The diol is bis-acylated using a suitable acylating agent such as acetyl chloride. The meso bis-acetated is enzymatically The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to herpes thymidine kinase, e.g., by competitive inhibition. Thus the compounds of this invention are commercial products to be sold for these purposes.

The compounds of the present invention are useful in the inhibition of herpes thymidine kinase, the treatment of infection by herpes virus and the treatment of consequent pathological conditions. Preventing or treating recurrent infection by herpes virus is defined as including, but not limited to, treating a wide range of states of herpes virus infection, including herpes simplex, primary herpetic dermatitis, eczema herpeticum, traumatic herpes, acute herpetic gingivostomatitis, recurrent stomatitis, acute herpetic rhinitis, herpetic infection of the genitalia, herpetic keratoconjunctivitis and keratitis, herpetic meningoencephalitis, vailcella, zoster or infection with CMV.

It will be understood that herpes virus herein includes any virus of the herpes family, including the following:

Herpes Simplex Virus-1 (HSV-1),

Herpes Simplex Virus-2 (HSV-2),

Varicella-Zoster Virus (VZV),

Cytomegalovirus (CMV), and

Epstein-Barr Virus.

The particular advantage of the compounds of this invention is their improved solubility compared to known related drugs.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating herpes infections and cold sores. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 100 mg/kg body weight in divided doses. One preferred dosage range is 0.1 to 10 mg/kg body weight orally in divided doses. Another preferred dosage range is 0.1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of herpes antivirals. For example, the compounds of this invention may be effectively administered, whether at periods of pre-exposure and/or post-exposure, in combination with effective amounts of the herpes antivitals or antiinfectives, such as those in the following Table.

TABLE

| ANTIVIRALS | | |
|---|---|---|
| Drug Name | Manufacturer | Indication |
| acyclovir | | herpes |
| penciclovir | SKB | herpes |

Acyclovir is synthesized by the methods in J. Antimicrob. Chemother., 12, Suppl. B (1983). Penciclovir, which is [3R]-9-(3,4-dihydroxybutyl)guanine, is synthesized by the methods in Harnden, et al., Drugs of the Future, 14, 3407 (1990).

EXAMPLE 1

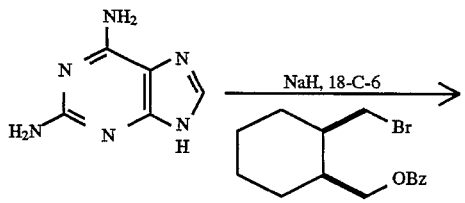

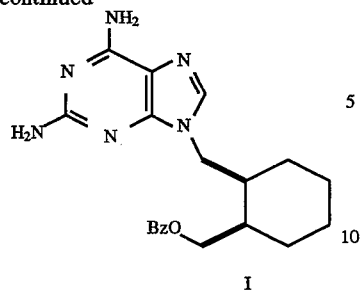

I

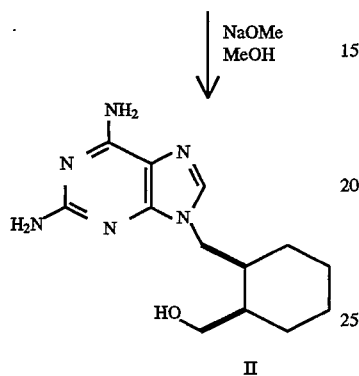

II

Preparation of 9-{[(Z)-2-(Benzoyloxymethyl)cyclohexyl]methyl}2,6-diaminopurine (I)

To a suspension of sodium hydride (0.75 eq) in DMF (7 mL) was added 2,6-diaminopurine (2 mmol). The mixture was warmed to 85° C. for 20 min cooled to room temperature and a catalydc amount of 18-crown-6 was added. The [(Z)-2-(Benzoyloxymethyl)cyclohexyl]-methyl bromide was added and the reaction warmed to 90° C. for 3 hours then cooled to 60° C. and stirred 12 hours longer. The reaction was cooled, neutralized with 1M HCl and concentrated to dryness. The residue was washed with water and filtered to collect the product as a colorless solid. $^1$HNMR (500 mHz, $d_6$DMSO): 8.5 ppm (bs,1H) 8.10 (s, 1H); 7.88 (d,2H); 7.63(t, 1H); 7.49(t, 2H); 7.40(bs, 2H); 4.30(m, 2H); 4.15–4.00(m, 2H), 2.39–2.13(m, 1H); 2.15–2.05(m, 1H), 1.70–1.20(m, 8H).

Preparation of 9-{[(Z)-2-(Hydroxymethyl)cyclohexyl]methyl}2,6-diaminopurine (II)

To a freshly prepared solution of sodium methoxide (2.5 eq) was added Compound I. The reaction was stirred at room temperature for 3 days, neutralized with acetic acid and concentrated to dryness. The residue was chromatographed on silica gel (chloroform:methanol:water 90:10:1) to give the desired product.

$^1$HNMR (500 mHz, $d_6$-DMSO): 8.05 ppm (s,1H); 6.89 (bs, 2H); 5.65(bs, 2H); 3.90(m, 2H); 3.55(t, 2H); 3.30(t, 2H, partially obscured by water); 2.20(bs, 1H), 1.75–1.10(m, 8H).

$^{13}$CNMR (125.8 mHz, $d_6$-DMSO):160.4, 156.3, 152.3, 133.2, 129.6, 128.9, 125.5, 113.5, 45.8, 26.4, 23.4, 8.9.

EXAMPLE 2

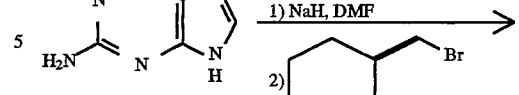

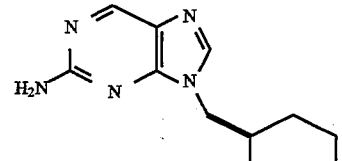

III

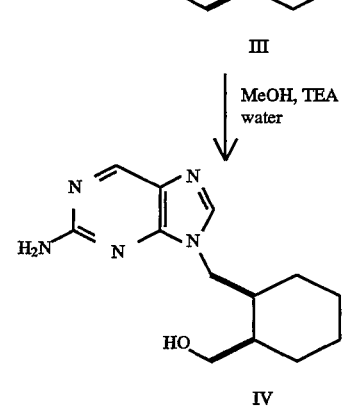

IV

Preparation of 9-{[(Z)-2-(Benzoyloxymethyl)cyclohexyl]methyl}2-aminopurine (III)

To a suspension of 2-aminopurine (1.5 mmol) in DMF (1.5 mL) was added sodium hydride (1.15 eq) and the mixture stirred at room temperature for 30 min. A solution of (Z)-2-(Benzoyloxymethyl)cyclohexyl]methyl bromide (1.1 eq) in DMF (0.5 mL) was added and the dark reaction warmed to 60° C. for 16 hours. The reaction was cooled and neutralized with acetic acid and concentrated to a tan solid. Purification by silica gel chromatography (2%–6% methanol in chloroform) gave the desired compound as a colorless foam. $^1$HNMR (500 mHz, $d_6$-DMSO): 8.52 ppm (s,1H); 8.09 (s, 1H); 7.92 (d, 2H); 7.62 (t, 1H); 7.50 (t, 2H); 7.41 (s, 2H); 4.42–4.25 (m, 3H 4.15 (t, 1H); 2.42 (bs, 1H); 2.13 (bs, 1H); 1.70–1.18(m, 8H).

Preparation of 9-{[(Z)-2-(Benzoyloxymethyl)cyclohexyl]methyl}2-amino-6-chloropurine (IV)

A solution of methanol (4 mL), water (4 mL), triethylamine (1 mL) and 9-{[(Z)-2-(Benzoyloxymethyl)cyclohexyl]methyl}2-aminopurine (0.3 mmol) was warmed to reflux for 12 hours, cooled and concentrated. The desired compound was purified by silica gel chromatography (chloroform:methanol 95:5). $^1$HNMR (500 mHz, $d_6$-DMSO):8.48 ppm (s, 1H); 8.05 (s, 1H); 6.42 (s, 2H); 4.10–3.95 (m, 2H), 3.57 (t, 1H); 3.28 (t, 1H, partially obscured by water), 2.30–2.23 (m, 1H); 1.78–1.10 (m, 10H).

EXAMPLE 3

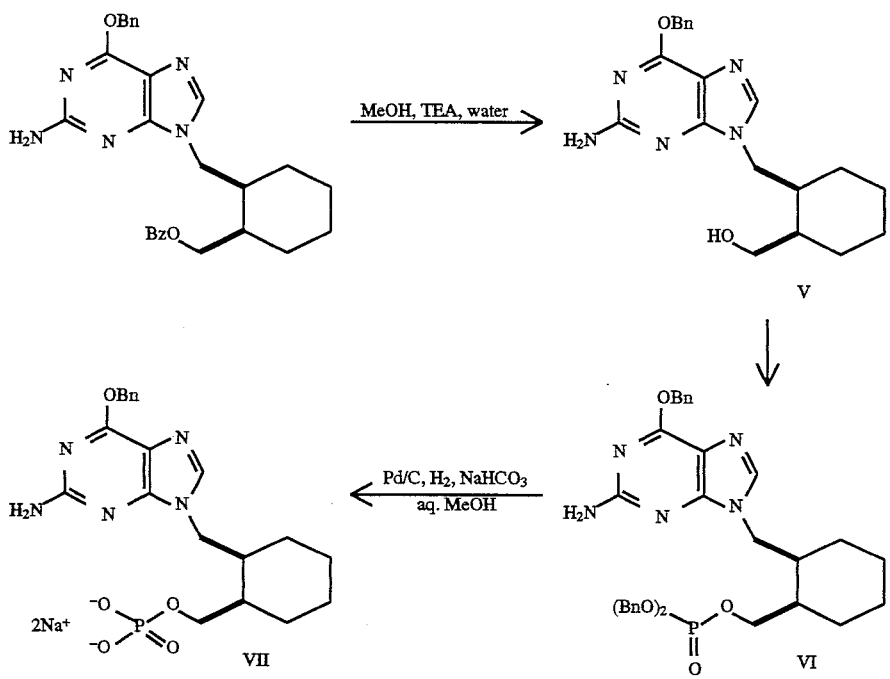

Preparation of 9-{[(Z)-2-(Hydroxymethyl) cyclohexyl]methyl}2-amino-6-benzyloxypurine (V)

A solution of 9-{[(Z)-2-(Benzoyloxymethyl)cyclohexyl] methyl}2-amino-6-benzyloxypurine (1.3 mmol), methanol (10 mL), water (10 mL) and triethylamine (2 mL) were warmed to reflux for 16 hours. The solution was cooled and concentrated. The desired compound was purified by silica gel chromatography (chloroform:acetone 4:1) to give a colorless foam. $^1$HNMR (500 mHz, $d_6$-DMSO); 8.40 ppm (s, 1H); 7.51 (d, 2H), 7.38 (t, 2H); 7.35 (t, 2H), 5.51 (s, 2H); 4.12–4.05 (m, 2H, partially obscured by water); 3.55 (dd, 1H); 2.28 (bs, 1H); 1.75–1.15 (m, 10H).

Preparation of 9-{[(Z)-2-(dibenzylphosphonomethyl)cyclohexyl]methyl}2-amino-6-benzyloxypurine (VI)

To a solution of 9-{[(Z)-2-(Hydroxymethyl)cyclohexyl] methyl}2-amino-6-benzyloxypurine (0.86 mmol) in dry THF (5 mL) was added t-butylmagnesium bromide (1.025 eq) and the solution stirred 10 minutes at room temperature. Tetrabenzylpyrophosphate (1.2 eq) was added and the reaction stirred 2.5 hours then quenched with 1M ammonium chloride and extracted with dichloromethane. This solution was washed with 1M sodium bicarbonate (×2), water and brine, dried and concentrated. The desired product was purified by silica gel chromatography (chloroform:methanol 95:5). $^1$HNMR (500 mHz, $d_6$-DMSO): 7.80 ppm (s, 1H); 7.45 (d, 2H); 7.42–7.25 (m, 13H); 6.40 (s, 2H); 5.45 (s, 2H); 5.03 (m, 4H); 4.15–4.08 (m, 1H), 4.00–3.86 (m, 3H); 2.23 (bs, 1H); 1.85 (bs, 1H); 1.64–0.95 (m, 8H).

Preparation of 9-{[(Z)-2-(phosphonomethyl) cyclohexyl]methyl}guanine-disodiumsalt (VII)

A suspension of methanol (3 mL), 1M sodium bicarbonate (0.3 mL, 2 eq), 9-{[(Z)-2-(dibenzylphosphonomethyl) cyclohexyl]methyl}2-amino-6-benzyloxypurine (0.15 mmol) and a catalytic amount of 10% Pd/C was stirred under a hydrogen balloon for 12 hours. The mixture was filtered and concentrated to yield the desired compound as a colorless solid. $^1$HNMR (500 mHz, $D_2O$): 7.82 (s, 1H); 4.08 (d, 2H); 3.92–3.80 (m, 1H); 3.80–3.72 (m, 1H); 2.30–2.18 (m, 1H); 2.04–1.96 (m, 1H); 1.64–1.15 (m, 8H).

EXAMPLE 4

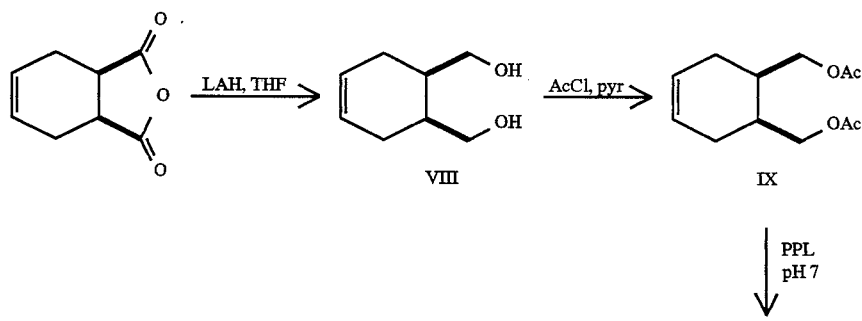

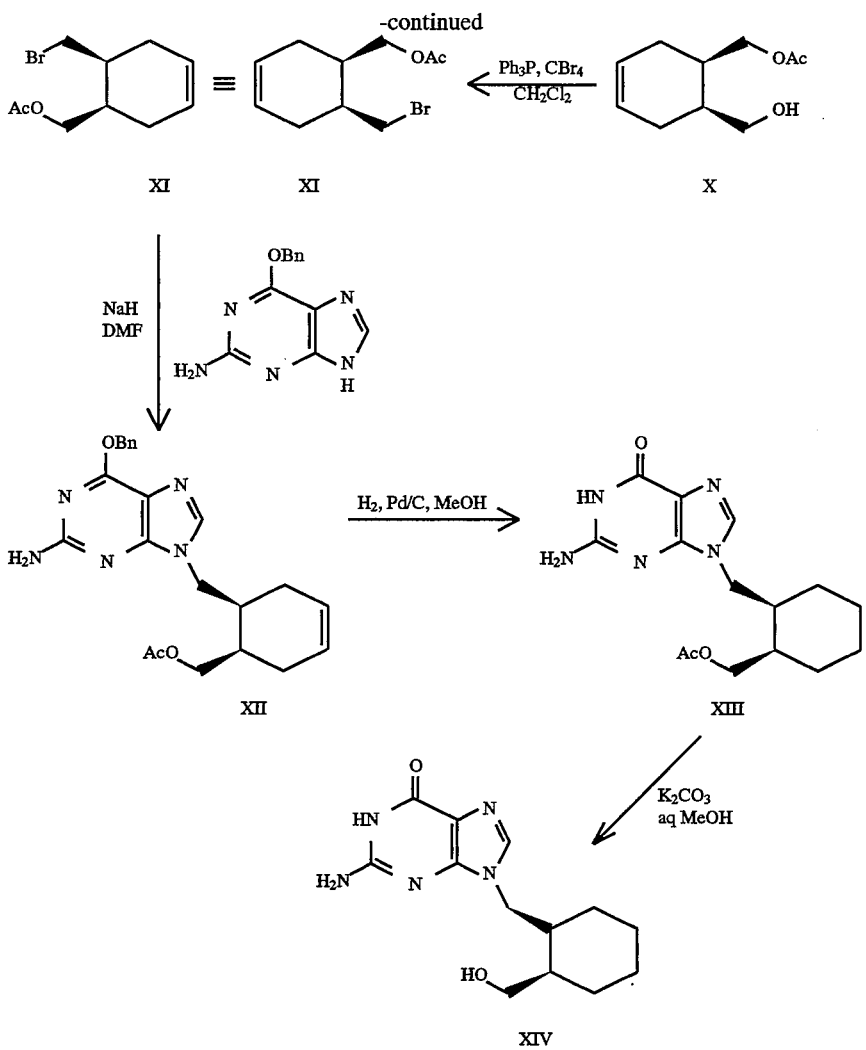

Preparation of cis-1,2-dihydroxymethylcyclohex-4-ene (VIII)

To a 0° C. suspension of lithium aluminum hydride (4 eq) in dry THF (250 mL) was added portionwise phtalic anhydride over 20 minutes. The mixture was brought to room temperature then warmed to reflux for 6 hours then cooled to 0° C. The reaction was quenched with saturated sodium sulfate solution, filtered and concentrated. The residue was taken into ethyl acetate washed with water, brine, dried and concentrated to yield the desired compound as a viscous oil. $^1$HNMR (500 mHz, CDCl$_3$): 5.62 ppm (s, 2H); 3.76–3.70 (m, 2H); 3.72–3.55 (m, 4H), 2.20–1.98 (m, 6H).

Preparation of cis-1,2-diacetoxymethylcyclohex-4-ene (IX)

To a solution of cis-1,2-dihydroxymethylcyclohex-4-ene (28.2 mmol), pyridine (3 eq) and dichloromethane (60 mL) was added acetyl chloride (2.1 eq). A colorless precipitate forms and the mixture stirred at room temperature overnight. The mixture was diluted with dichloromethane and washed with water, 1N hydrochloric acid (x2), brine, dried and concentrated to a slightly orange oil. $^1$HNMR (500 mHz, CDCL$_3$): 5.64 ppm (s, 2H); 4.12–4.07 (m, 2H); 4.04–3.98 (m, 2H); 2.29–2.12 (m, 4H); 2.03 (s, 6H), 1.96–1.88 (m, 2H).

Preparation of 1(R)-acetoxymethyl-2(S)-hydroxymethylcyclohex-4-ene (X)

A suspension of cis-1,2-diacetoxymethylcyclohex-4-ene (10 mmol), pH 7 phosphate buffer (25 mL) porcine pancreatic lipase (200 mg, Sigma Type II) was vigorously stirred. The reaction was kept constant by addition of 1M sodium hydroxide from a pH controller and syringe pump. After 16 hours addition of 1 eq hydroxide was complete and the mixture was filtered through a pad of Celite. The Celite was washed with ether and the filtrates were washed with ether (x3). The combined ether washes were washed with brine, dried and concentrated to yield the desired compound as a slightly yellow oil.

α$_D$=–17° (c=0.42, chloroform) $^1$HNMR (500 mHz, CDCl$_3$): 5.68–5.60 ppm (m, 2H); 4.21 (dd, 1H); 3.95 (dd, 1H); 3.68 (dd, 1H); 3.57 (dd, 1H); 2.29–2.12 (m, 4H); 2.05 (s, 3H).

Preparation of 1(R)-acetoxymethyl-2(S)-bromomethylcyclohex-4-ene (XI)

To a solution of dichloromethane (20 mL), tetrabromomethane (1.5 eq) and 1(R)-acetoxymethyl-2(S)-hydroxymethylcyclohex-4-ene (6.8 mmol) was added a solution of triphenylphosphine (1.2 eq) in dichloromethane (5 mL) and the reaction stirred in the dark for four days. The reaction was concentrated to a dark oil and triturated with ether. The solid was filtered and the filtrate concentrated and purified by silica gel chromatography to yield the desired compound as a colorless oil. $^{1}$HNMR (500 mHz), CDCl$_3$): 5.64 ppm (dd, 2H), 4.09–4.0 (m, 2H); 3.48 (dd, 1H); 3.38 (t, 1H); 2.08 (s, 3H).

Preparation of 9-{[1(R)-acetoxymethyl-2(S)-cyclohex-4-enyl]-methyl}2-amino-6-benzyloxypurine (XII)

To a suspension of 2-amino-6-benzyloxypurine (1 mmol) in DMF (2 mL) was added sodium hydride (1.15 eq) and the mixture stirred at room temperature for 30 minutes. A solution of 1(R)-acetoxymethyl-2(S)-bromomethylcyclohex-4-ene (1.1 eq) in DMF (0.75 mL) and the reaction stirred at 60° C. for 16 hours. The reaction was neutralized with acetic acid and concentrated. The desired compound was purified by silica gel chromatography (chloroform:methanol 95:5) as a colorless foam. $^{1}$HNMR (500 mHz, CDCl$_3$): 8.02 ppm (s, 1H); 7.65 (s, 1H); 7.49 (d, 2H); 7.38–7.26 (m, 3H); 5.65 (dd, 2H); 5.56 (s, 2H); 4.33 (dd, 1H); 4.12 (dd, 1H); 4.06–3.97 (m, 2H); 2.40 (bs, 1H); 2.23–1.75 (m, 6H); 2.20 (s, 3H).

Preparation of 9-{[1(R)-acetoxymethyl-2(S)-cyclohexyl]methyl}guanine (XIII)

A suspension of 9-{[1(R)-acetoxymethyl-2(S)-cyclohex-4-enyl]methyl}2-amino-6-benzyloxypurine (0.75 mmol), ethanol (5 mL) and a catalytic amount of 10% Pd/C was stirred under a hydrogen balloon for 3 hours. The reaction was filtered and concentrated to yield the desired compound. $^{1}$HNMR (500 mHz, d$_6$DMSO): 10.80 ppm (bs, 1H); 7.65 (s, 1H); 6.48 (s, 2H); 4.15–3.88 (m, 4H); 2.23 (bs, 1H); 2.01 (s, 3H); 1.92 (m, 1H); 1.68–1.15 (m, 8H).

Preparation of 9-{[1(R)-hydroxymethyl-2(S)-cyclohexyl]methyl}guanine (XIV)

A solution of 9-{[1(R)-acetoxymethyl-2(S)-cyclohexyl]methyl}guanine (0.75 mmol), aqueous methanol (2 mL) and potassium carbonate (3 eq) were stirred at room temperature for 3 hours. The reaction was concentrated and the desired compound purified by silica gel chromatography (chloroform:methanol:water 90:10:1). $^{1}$HNMR (500 mHz, d$_6$-DMSO); 10.44 ppm (bs, 1H); 7.66 (s, 1H); 6.39 (bs, 2H); 4.46 (t, 2H); 3.90 (m, 2H), 3.55–3.30 (m, 2H, partially obscured by water); 2.18 (m, 1H); 1.8–1.1 (m, 9H).

ASSAY FOR INHIBITION OF HERPES THYMIDINE KINASE

The assay mixture contains in a final volume of 110 microliters the following: 50 mM Tris-HCl, pH 7.5; 5 mM MgCl$_2$; 5 mM ATP; 2 mM dithiothreitol (DTT); 2.5 mM KF; 0.25 mg/ml bovine serum albumin (BSA); 2 mM thymidine labeled with either $^{14}$C or $^{3}$H; the compound being tested as inhibitor; and the viral thymidine kinase. The amount of enzyme, incubation time and temperature are adjusted so that no more than 20% of the substrate is converted to product in a reaction without inhibitor. At the end of the incubation period, 100 microliters of the assay mixture are spotted on a 25 mm disk of DEAE paper. The disks are washed three times with ethanol to remove unreacted thymidine and the amount of thymidine monophosphate produced is determined by scintillation counting of the disks. The results (in IC$_{50}$) are calculated to give the concentration of inhibitor resulting in 50% inhibition of enzyme. The IC$_{50}$ of L-58,340 is about 100 nM.

IN VITRO METABOLISM

1. Homogenize 1.3 ml of plasma with 0.380 ml of buffer A (* Buffer A: 50 mM KPO$_4$ (pH 7.4)–5 mM DTT) or homogenize 0.42 g of Tissue with 1.260 ml of buffer A*.
2. Combine:
   1680 µl of the homogenate
   1800 µl of buffer A*
   120 µl of the test compound (1.5 mg/ml in 50% methanol).
3. Immediately remove zero time sample (0.6 ml).
4. Incubate the rest at 37° C.
5. Remove 0.6 ml aliquots at 30, 60, 120 and 180 min. freeze.
6. Add each aliquot to a tube containing 0.6 ml methanol. Vortex well.
7. Centrifuge. Remove 0.6 ml and 0.2 ml of the supernatant.
8. Dry down by vacuum centrifugation.
9. Resuspend the 0.6 ml residues in 10% acetonitrile.
10. Chromatograph one half of the resuspended residues.
11. Assay a proper dilution of the 0.2 residue in the TK assay.

Results indicate that the preferred compounds of the present invention are substrates for xanthine oxidase or deaminase or phosphatase, and they function as prodrugs.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A [1S,2R] compound, which is

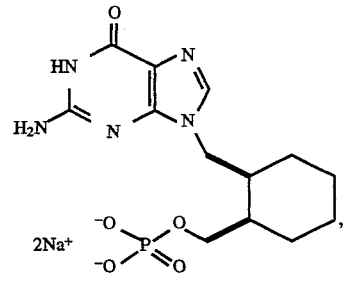

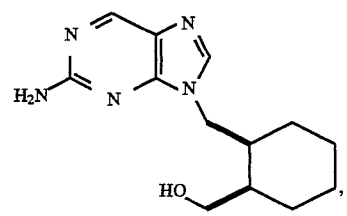

or

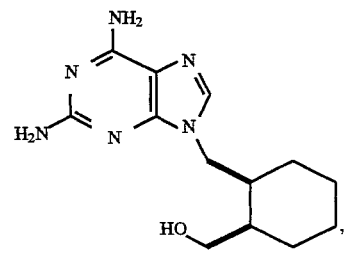

or a pharmaceutically acceptable salt or hydrate thereof.

2. A [1S,2R] compound which is

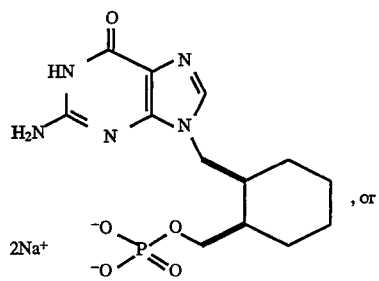

VII

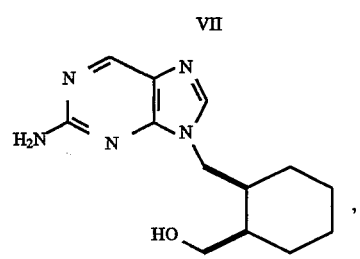

or a pharmaceutically acceptable salt or hydrate thereof.

3. A method of inhibiting herpes thymidine kinase, comprising administering to a mammal an effective amount of a compound as in any one of claims 1 or 2.

4. A method of preventing recurrent infection of herpes virus, comprising administering to a mammal an effective amount of a compound as in any one of claims 1 or 2.

5. A pharmaceutical composition useful for inhibiting herpes virus thymidine kinase or for preventing recurrent infection of herpes infection, comprising an effective amount of a compound as in any one of claims 1 or 2, and a pharmaceutically acceptable carrier.

6. A combination of a compound of claim 2 and acyclovir.

* * * * *